United States Patent [19]
Ichikawa et al.

[11] Patent Number: 5,447,624
[45] Date of Patent: Sep. 5, 1995

[54] PACKINGS FOR LIQUID CHROMATOGRAPHY AND PROCESS FOR PRODUCING THE SAME

[75] Inventors: Takanobu Kawai; Hiroshi Wakizaka, Hiroshi Ichikawa, Akira Yokoyama, Takanobu Kawai, Hiroshi Wakizaka, of Yokohama; Hiroyuki Moriyama, Kudamatsu; Katsuo Komiya, Hikari, all of Japan

[73] Assignees: Nippon Carbon Co., Ltd., Tokyo; Tosoh Corporation, Yamaguchi, both of Japan

[21] Appl. No.: 223,696

[22] Filed: Apr. 6, 1994

[30] Foreign Application Priority Data

Apr. 9, 1993 [JP] Japan .................................. 5-105904

[51] Int. Cl.⁶ .............................................. B01D 15/08
[52] U.S. Cl. .................................. 210/198.2; 210/502.1; 210/656; 502/407; 502/416; 502/417; 502/430; 502/432; 502/439
[58] Field of Search ............... 502/416, 407, 417, 423, 502/430, 432, 439; 210/635, 656, 198.2, 502.1

[56] References Cited

U.S. PATENT DOCUMENTS

| | | | |
|---|---|---|---|
| 3,935,299 | 1/1976 | Kiselev | 502/407 |
| 4,472,332 | 9/1984 | Fukushima et al. | 264/44 |
| 4,777,153 | 10/1988 | Sonuparlak et al. | 501/82 |
| 4,837,195 | 6/1989 | Cox | 502/407 |
| 4,871,693 | 10/1989 | Kagaku | 501/9 |
| 5,019,270 | 5/1991 | Afeyan | 210/656 |
| 5,098,576 | 3/1992 | Cabrera | 210/656 |
| 5,228,989 | 7/1993 | Afeyan | 210/198.2 |
| 5,384,042 | 1/1995 | Afeyan | 210/198.2 |

FOREIGN PATENT DOCUMENTS

| | | | |
|---|---|---|---|
| 0314142 | 5/1989 | European Pat. Off. | 210/198.2 |
| 0368138 | 5/1990 | European Pat. Off. | 210/198.2 |

Primary Examiner—Ernest G. Therkorn
Attorney, Agent, or Firm—Bucknam and Archer

[57] ABSTRACT

A microspherical packing for liquid chromatography, which comprises a porous silicon carbide having numerous through-pores, and a process for producing said microspherical packing.

8 Claims, 3 Drawing Sheets

PACKINGS FOR LIQUID CHROMATOGRAPHY AND PROCESS FOR PRODUCING THE SAME

BACKGROUND OF THE INVENTION

1. Field of the Invention

The present invention relates to a packing for liquid chromatography, and a process for producing the same. In particular, the present invention relates to a microspherical packing for liquid chromatography, which comprises a porous silicon carbide having numerous through-pores, and a process for producing the same.

2. Prior Art

Packings or adsorbents used hitherto for liquid chromatography include those based on a silica gel such as ODS silica gel and those based on synthetic resins.

Such silica gel-based packings are superior in that they have relatively high mechanical strength and high separation power. In addition, since they undergo only slight swelling or shrinkage in various organic solvents, they can easily be changed in use for analysis conditions with different eluents. However, they have defects that they are poor in chemical resistance in alkaline and acidic regions and are also poor in thermal resistance.

On the other hand, although such synthetic resin-based packings have high chemical resistance, they are defective in that they have low mechanical strength and they are swollen or shrunk in a solvent due to their low solvent resistance thereby to make it difficult for them to change in use for analysis conditions with different eluents.

Carbonaceous packings are also known as packings for conventional liquid chromatography. The carbonaceous packings are chemically stable and have high mechanical strength and such features that ODS silica gel and the like do not possess, since the carbonaceous packings are covered on their whole surface with $\pi$-electrons. However, the carbonaceous packings have strong power of adsorbing particularly polycyclic aromatic compounds since they are covered with $\pi$-electrons as described above, and, therefore, they have defects that they will cause an elution time to be prolonged too much depending on samples used to be chromatographed, will cause remarkable tailing to occur, or will cause the elution to become impossible.

SUMMARY OF THE INVENTION

The present invention aims at solving the abovementioned problems of the prior art, and an object of the present invention is to provide packings or adsorbents for liquid chromatography which have excellent chemical, thermal and solvent resistances, also have an non-excessive active surface and are capable of separating rapidly without fail even any samples, particularly protein or a compound having qelectrons such as a polycyclic aromatic compound, without too tightly adsorbing the sample onto their surface. Further, another object of the present invention is to provide a process for producing the packings mentioned above.

In attempts to achieve the above objects, the present inventors made intensive studies and found that these objects can be attained by using a silicon carbide having excellent chemical resistance (to acids and alkalis), solvent and thermal resistances and high mechanical strength as a material for the packing for liquid chromatography. The present invention is based on the above finding.

The packing for liquid chromatography of the present invention is a microspherical one which comprises a porous silicon carbide having numerous through-pores. Although the properties to be possessed by the packing of the present invention may suitably be selected depending on a sample to be analyzed, particularly preferable is one having a particle diameter of 2 to 200 μm, a pore diameter of 3 to 200 nm as determined by the mercury porosimeter method, a pore volume of 0.1 to 3.0 ml/g as determined by said method, a specific surface area of 10 to 600 m$^2$/g as determined by said method and a desorption-side specific surface area of 5 to 650 m$^2$/g as determined by the BJH method, since it exhibits a particularly high separating efficiency. The BJH method is a known method usually employed for determining desorption-side specific surface areas and is described in detail by E. P. Barrett, L. G. Joynet and P. P. Halenda in Journal of American Chemical Society, Vol. 73, No. 1, pages 373 to 380 (January, 1951).

The packing for liquid chromatography of the present invention comprising silicon carbide which is free from residual SiO$_2$, will, per se, not substantially adsorb protein and a compound having $\pi$-electrons, such as a polycyclic aromatic compound. Thus, the silicon carbide comprised in the packing is preferably free from residual SiO$_2$ because it will adsorb said protein and compound to some extent if SiO$_2$ remains even in a very small amount therein.

The silicon carbide constituting the packing for liquid chromatography of the present invention may be in the form of porous microspheres having numerous through-pores. The silicon carbide produced by forming a polycarbosilane and then baking (firing) the formed polycarbosilane ls preferred with β-SiC being particularly preferred.

Although any specific processes for producing the porous silicon carbide by forming and baking a polycarbosilane are not particularly limited, the porous silicon carbide having the desired properties can be efficiently and easily obtained by the processes of the present invention which will be described below.

There will now be made a description of various processes for producing the packing for liquid chromatography of the present invention.

A first process for producing the packing for liquid chromatography of the present invention comprises the steps of mixing a polycarbosilane, carbon black and a solvent together to obtain a slurry, granulating the slurry into spherical particles, heating the spherical particles to 1450° to 1650° C. at a temperature elevation rate of 100° to 300° C./h in an inert atmosphere to bake the polycarbosilane, and holding the baked spherical particles at 500° to 800° C. in air for 15 to 120 h to remove carbon black by oxidation.

The polycarbosilane used in the present process is preferably one having a number-average molecular weight of 500 to 20,000. A polycarbosllane having a number-average molecular weight of below 500 has a viscosity insufficient for obtaining spherical particles. Therefore the resultant particles are amorphous, the baking of them is difficult and the baking yield is low unfavorably. On the contrary, a polycarbosilane having a number-average molecular weight of above 20,000 is also unsuitable because it is insoluble in a solvent and is thus substantially unusable. The particle diameter of the carbon black used in the present process is selected depending on, for example, the desired pore diameter of the resulting packing. The average particle diameter of the carbon black is preferably in the range of 12 to 60 μm. When the average particle diameter is below 12 μm, the pore diameter of the obtained packing tends to become too small for a substance being analyzed to enter the pores, while when it exceeds 60 μm, the pore diameter of the obtained packing tends to become too large to secure a sufficient specific surface area. The solvents used in the present process are preferably toluene, cyclohexane, n-hexane, and the like.

The mixing ratio among the polycarbosilane, carbon black and solvent for the formation of a slurry is suitably selected depending on the intended pore volume and the like of the resulting packing, and it is preferably in the range of 1:0.8 to 1.2:2.5 to 3.5 by weight. Any ratios or proportions outside this range tend to result in producing a packing having an undesired pore volume, a low strength and an undesirable shape.

In conducting the granulation according to the present invention, a spray granulation method or a wet (emulsion) granulation method is preferred for obtaining spherical particles. The former is a method for producing spherical particles by spraying the aforesaid slurry under heating to evaporate the solvent therefrom. The latter is a method for producing spherical particles by adding said slurry to a warm dispersing solvent immiscible therewith for mixing them together. The diameter of the spherical particles obtained in the above granulation step is selected depending on the desired particle diameter and the like of the packing to be obtained. It is preferably 3 to 250 μm when the desired particle diameter of the resulting packing is 2 to 200 μm.

In the process of the present invention, it is necessary that the spherical particles be heated to 1450° to 1650° C. at a temperature elevation rate of 100° to 300° C./h in an inert atmosphere such as an argon atmosphere to bake the polycarbosilane within the spherical particles. Unless the baking is conducted in an inert atmosphere, it will be impossible to obtain silicon carbide by thoroughly removing hydrocarbons and hydrogen from the polycarbosllane. If the baking temperature is below 1450° C., the crystallization of silicon carbide will be insufficient and, on the contrary, if it exceeds 1650° C., the crystallization will be excessively accelerated to impair the strength of the resulting packing. Although the baking is possible even when the temperature elevation rate is below 100° C./h, the baking in this case will take a long time thereby to increase the cost. On the contrary, when it exceeds 300° C./h, the thermal decomposition speed of the polycarbosilane will be so high that excessive degassing results.

In addition, the above-described process of the present invention may preferably further comprise the step of infusibilizlng the spherical particles by heating them to 110° to 180° C. at a temperature elevation rate of 15° to 30° C./h in air prior to the baking step. By thus heating the spherical particles under these conditions, the polycarbosilane surface is oxidized and thereby infuslbilized to prevent the deformation of the particles in the subsequent baking step.

Next, it is necessary in the process of the present invention to maintain the above baked spherical particles at 500° to 800° C. in air for 15 to 120 h to remove the carbon black therefrom by oxidation and combustion. By thus removing the carbon black portion from the spherical particles to leave only the silicon carbide portion, microspheres comprising porous silicon carbide having numerous through-pores can be obtained.

When the temperature is below 500° C., the complete removal of the carbon black is difficult and, on the contrary, when it exceeds 800° C., the oxidation proceeds excessively and the amount of $SiO_2$ formed is increased unfavorably. When the maintaining time is below 15 h, the removal of carbon black is insufficient and, on the contrary, when it exceeds 120 h, only the silicon carbide portion is still heated after the complete removal of carbon black, this being substantially wasteful and unnecessary.

The above-described process of the present invention preferably comprises a further step of removing residual $SiO_2$ by washing posterior to the step of removing the carbon black. In this further step, the residual $SiO_2$ is removed by washing with NaOH, hydrofluoric acid or the like. By thus completely removing the residual $SiO_2$, the above-mentioned adsorption of protein or a compound having $\pi$-electrons, such as a po].ycyclic aromatic compound, can be prevented without fail.

There will now be made a description of a second process for producing the packing for liquid chromatography of the present invention.

This second process comprises the steps of impregnating porous spherical carbon particles with a polycarbosilane, heating the particles thus impregnated to 1450° to 1650° C. at a temperature elevation rate of 100° to 300° C./h in an inert atmosphere to bake the polycarbosllane, and holding the baked particles at 500° to 800° C. in air for 15 to 120 h to remove the carbon portion therefrom by oxidation.

The term "porous spherical carbon particles" used herein refers to porous spherical particles of a carbonaceous material (carbon or graphite) having a pore volume of preferably at least 0.25 ml/g. When the pore volume is below 0.25 ml/g, the strength of the obtained silicon carbide packing tends to be insufficient. The diameter of the porous spherical carbon particle is selected depending on the desired particle diameter of the resulting packlng, and is preferably 5 to 200 μm.

The porous spherical carbon particles are produced by, for example, granulating a mixture of (i) carbon black, (ii) (a) a synthetlc resin which can be carbonized by heating and/or (b) toluene- or benzene-solubles of pitch and (iii) an organic solvent, then infusibilizing the resultant particles, if necessary, and baking them in an inert atmosphere. The synthetic resins which can be carbonized by heating include phenol, furan, furfural, divinylbenzene and urea resins.

The porous spherical carbon particles per se have hitherto been used as a carbonaceous packing for liquid chromatography. They are described in detail in, for example, Japanese Patent Application Laid-Open Gazettes Nos. Hei 4-169844 (169844/92) and Hei 4-357183 (357183/92).

In the second process of the present invention, it is necessary to first impregnate the above-described porous spherical carbon particles with a polycarbosilane. The impregnation is conducted preferably by dissolving a polycarbosilane in & solvent such as xylene, tetrahydrofuran (THF), hexane or cyclohexane, controlling the viscosity of the solution, and impregnating the porous spherical carbon particles degassed in a vacuum with the above solution under pressure so that the solution penetrates into the pores. The polycarbosilane to be used is similar to the one used in the first process.

Next, it is necessary in the second process of the present invention to bake the particles impregnated with the polycarbosilane and then remove the carbon portion therefrom by oxidation. These treatments are conducted under the same conditions as those of the above-described first process. By thus removing the carbon portion from the particles impregnated with the polycarbosilane and then burned in order to leave only the silicon carbide portion, microspheres comprising porous silicon carbide having numerous through-pores can be obtained.

Also the second process of the present invention preferably further comprises the step of infusibilizing the particles impregnated with the polycarbosilane, by heating them to 110° to 180° C. at a temperature elevation rate of 15° to 30° C./h in air prior to the baking step, as in the first process. This second process preferably comprises a further step of removing residual $SiO_2$ by washing posterior to the step of removing the carbon portion, as in the first process.

There will now be made a description of a third process for producing the packing for liquid chromatography of the present invention.

This third process comprises the steps of infusibilizing a polycarbosilane by heating it to 110° to 180° C. at a temperature elevation rate of 15° to 30° C./h in air, pulverizing the infusibilized polycarbosllane into polycarbosilane powder, mixing the polycarbosilane powder with a polycarbosilane and a solvent to obtain a slurry, granulating the slurry into spherical particles, infusibilizing the spherical particles by heating them to 110° to 180° C. at a temperature elevation rate of 15° to 30° C./h in air, and heating the infusibllized particles to 1450° to 1650° C. at a temperature elevation rate of 100° to 300° C./h in an inert atmosphere to bake the polycarbosilane.

In the third process, the polycarbosilane is firstly infusibilized by heating it to 110° to 180° C. at a temperature elevation rate of 15° to 30° C./h in air and then pulverized into polycarbosilane powder. By infusibilizing the polycarbosilane under the above-described conditions, it is hardened to make the ultrafine pulverization thereof possible. The polycarbosilane to be used in this step is similar to the one used in the first process. The particle diameter of the polycarbosilane powder is selected depending on the desired pore diameter of the obtained packing. The average particle diameter of the above powder is preferably 0.05 to 0.5 μm, more preferably about 0.1 μm.

Then the polycarbosilane powder so obtained is mixed with a polycarbosilane and a solvent to obtain a slurry. The polycarbosilane and the solvent used in this step are also similar to those used in the first process. The mixing ratio among the polycarbosilane powder, polycarbosilane and solvent is suitably selected depending on the intended pore volume and the like of the resulting packing. Said mixing ratio is preferably in the range of 1:0.05 to 0.2:1.5 to 2.5 by weight. Any ratios or proportions outside this range tend to result in producing a packing having an undesired pore volume, a low strength and an undesirable shape.

In the third process of the present invention, it is necessary that the above-described slurry be granulated, infusibilized and then baked. These treatments are conducted under the same conditions as those of the first process. By thus infusibilizing and then baking the spherical particles obtained by granulating the polycarbosilane solution in which the polycarbosilane powder is dispersed, the polycarbosilane is converted into silicon carbide without suffering deformation at the time of burning thereby to form microspheres comprising porous silicon carbide hawing numerous through-pores. It is preferred that this process further comprise the step of removing residual $SiO_2$ by washing posterior to the burning step, as in the first process.

The packing of the present invention is usable as it is for an aqueous or non-aqueous GPC. In addition, when the surface of the packing is chemically modified by a well-known method, the packing can be useful for various liquid chromatographies for other uses such as reversed phase liquid chromatography and ion exchange liquid chromatography.

DESCRIPTION OF THE PREFERRED EMBODIMENTS

The following Examples will further illustrate the present invention in comparison with the following Comparative Examples.

EXAMPLE 1

100 parts by weight of carbon black having an average partlcle dlameter of 12 nm, a DBP oil absorption of 113 ml/100 g and a specific surface area of 85 $m^2/g$ as determined by the BET method with use of $N_2$ gas, 100 parts by weight of a polycarbosilane having a number-average molecular weight of 1,500 and 300 parts by weight of toluene were fed into a ball mill and homogeneously mixed together to obtain a slurry, which was spray-granulated with a spray dryer to obtain spherical particles.

Then the spherical partlcles were heated to 160° C. at a temperature elevation rate of 15° C./h in air, held at that temperature for 5 min. to infuslbllize them, heated to 1500° C. at a temperature elevation rate of 200° C./h in an argon gas atmosphere and kept at that temperature for 1 h to be baked, thereby converting the polycarbosilane within the particles into silicon carbide. Thereafter, the baked spherical particles were held at 700° C. for 50 h in air to remove the carbon black by complete combustion thereof, thereby obtaining porous microspheres. The porous mlcrospheres thus obtained were washed with an aqueous solution of sodium hydroxide to remove residual $SiO_2$, dried and classified to obtain porous microspheres having a diameter of 3 to 8 μm.

The properties of the porous microspheres were measured with a mercury poroslmeter with the result that the pore volume was 0.36 ml/g, the specific surface area was 120 $m^2/g$ and the average pore diameter was 11.6 nm. The desorption-slde specific surface area measured by the BJH method was 92 $m^2/g$. The porous microspheres thus obtained were analyzed by X-ray diffractometry to find only the peak of β-SiC. These facts indicated that the porous microspheres obtained above were silicon carbide microspheres having numerous through-pores.

Figure 1:
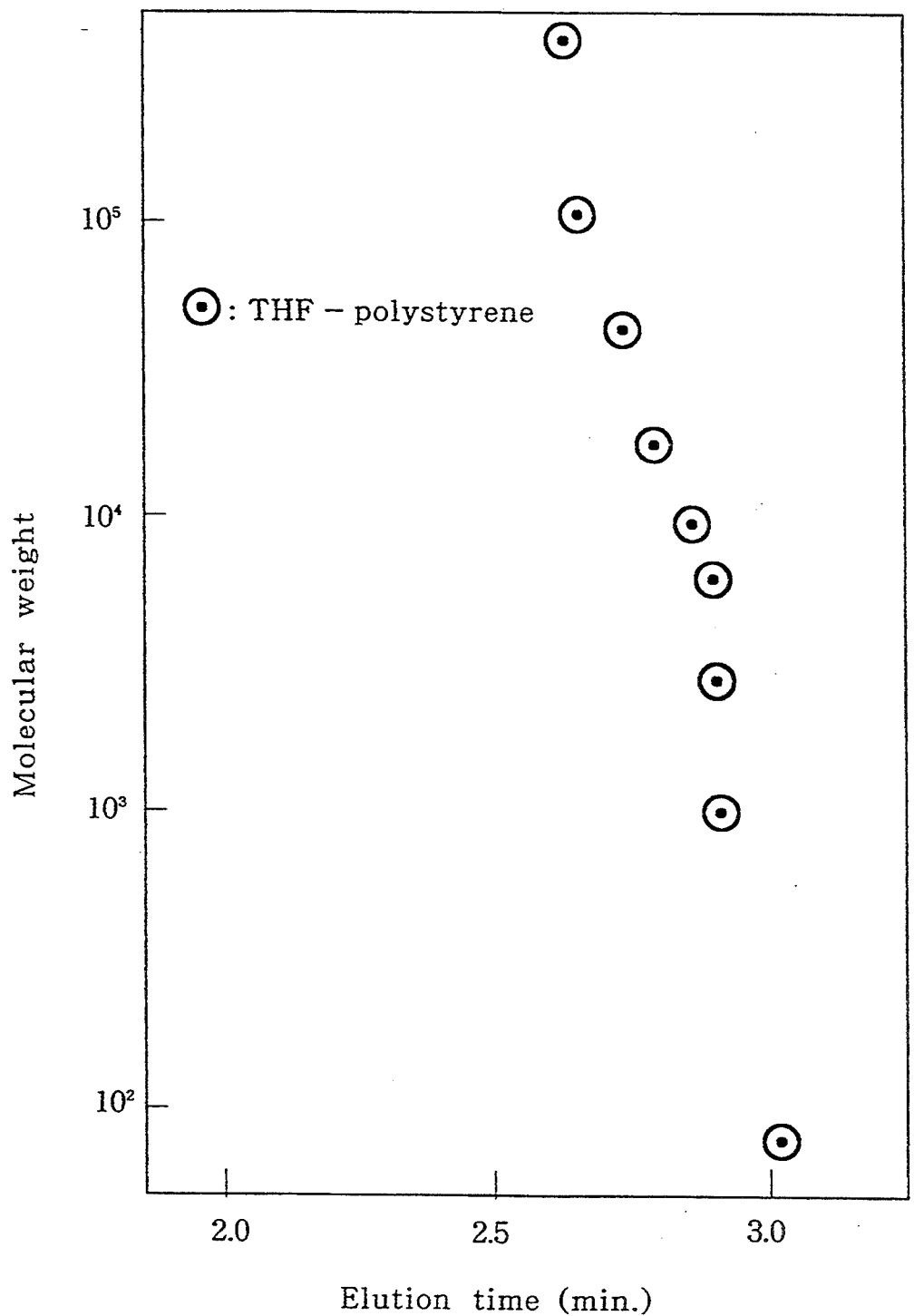
FIG. 1 is a graph showing the results of analysis of standard polystyrene samples with use of the packing of the present invention obtained in Example 1.

The silicon carbide microspheres were fed as a packing into a stainless steel column having an inner diameter of 4.6 mm and a length of 100 mm. Several samples of standard (reference) polystyrenes each having a known molecular weight were analyzed with the above microspheres as the packing and tetrahydrofuran as the eluent [flow rate: 0.5 ml/min., pressure: 3 kg/cm², detector: ultraviolet absorptiometer (detection wavelength: 254 nm) and temp.: 25° C.] thereby to obtain the results shown in FIG. 1. It will be apparent from FIG. 1 that when the packing of the present invention produced in this Example was used, there was obtained an excellent calibration curve for polystyrenes having a molecular weight in the range of $2 \times 10^3$ to $2 \times 10^5$.

EXAMPLE 2

100 parts by weight of carbon black having an average particle diameter of 30 nm, a DBP oil absorption of 95 ml/100 g and a specific surface area of 430 m²/g as determined by the BET method with $N_2$ gas, 90 parts by weight of a liquid phenol resin and 230 parts by weight of methanol were homogeneously mixed together to obtain a slurry, which was spray-granulated with a spray dryer and then hardened by holding the resultant particles at 140° C. for 60 min. The particles so hardened were then baked (by heating to 1,000° C. at a temperature elevation rate of 200° C./h, keeping that temperature for 30 min., further heating to 2,000° C. gradually during a period of 1 h and keeping that temperature for 15 min.) in an inert atmosphere to obtain porous spherical carbon particles (porous carbon spheres). The obtained carbon particles had a diameter of 3 to 10 μm, a pore volume of 0.35 ml/g and an average pore diameter of 55 nm.

Then, a polycarbosilane having a number-average molecular weight of 1500 was dissolved in xylene to obtain a polycarbosilane solution, after which the porous spherical carbon particles degassed in a vacuum were impregnated with the polycarbosilane solution under an elevated pressure so that the solution penetrates into the pores. Subsequently, the xylene in the solution was removed by the use of an evaporator to impregnate the porous spherical carbon particles with the polycarbosilane. The particles thus impregnated were heated to 1520° C. at a temperature elevation rate of 200° C./h in an argon gas atmosphere and held at that temperature for 30 min. to bake the particles, thereby converting the polycarbosilane Into silicon carbide. Thereafter, the baked particles were held at 700° C. for 50 h in air to completely remove the carbon portions from the particles by oxidation, thereby obtaining grayish green porous microspheres. The porous microspheres thus obtained were washed with an aqueous sodium hydroxide solution to remove residual $SiO_2$ and then dried.

The porous microspheres thus obtalned had a particle diameter of 2 to 11 μm. The properties of the porous microspheres were measured with a mercury porosimeter to find that the pore volume was 0.50 ml/g, the specific surface area was 78 m²/g and the average pore diameter was 20 nm. The desorption-side specific surface area as determined by the BJH method was 75 m²/g. The porous microspheres thus obtained were analyzed by X-ray diffractometry to find only the peak of β-SiC. These facts indicated that the porous microspheres obtained above were silicon carbide microspheres having numerous through-pores.

The silicon carbide microspheres were filled into a stainless steel column having an inner diameter of 4.6 mm and a length of 150 mm. Samples of standard polystyrenes were analyzed with the above microspheres as the packing and chloroform or tetrahydrofuran as the eluent thereby to obtain the results shown in FIG. 2. It will be apparent from FIG. 2 that when the packing of the present invention produced in this Example was used, there were obtained excellent calibration curves for polystyrenes having a molecular weight in the range of $8 \times 10^3$ to $1 \times 10^6$ when either of said solvents was used as the eluent.

Figure 2:
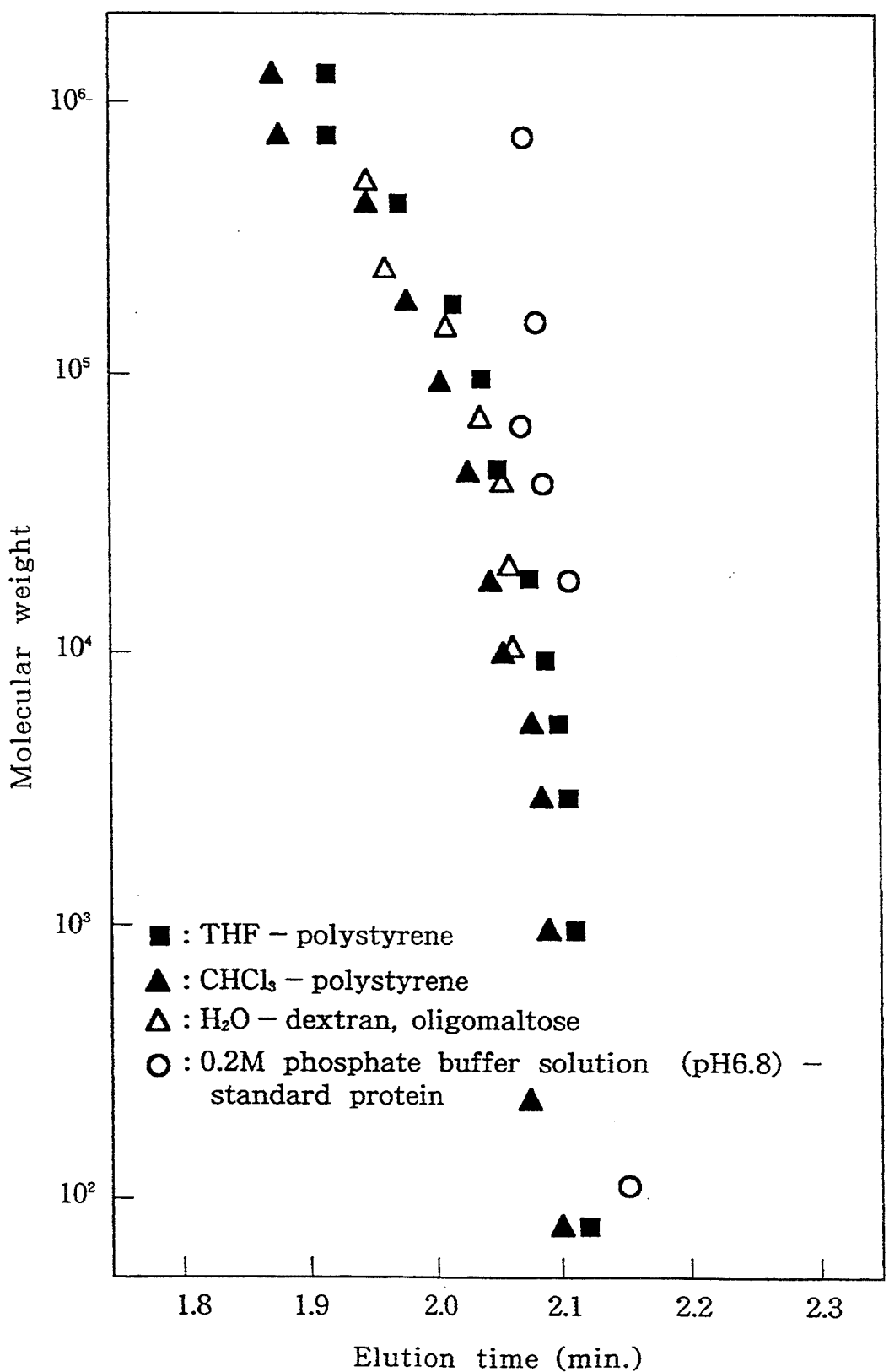
FIG. 2 is a graph showing the results of analysis of standard polystyrene, standard saccharide and standard protein samples with use of the packing of the present invention obtained in Example 2.

When several samples of dextrans and oligomaltoses each having a known molecular weight were analyzed with the above microspheres as the packing and water as the eluent by means of a differential refractometer thereby to obtain excellent calibration curves for the samples having a molecular weight in the range of $2 \times 10^4$ to $2 \times 10^5$ as shown in FIG. 2.

Further, the analyses of standard proteins which were thyroglobulln (molecular weight: 660,000), γ-globulin (molecular weight: 150,000), bovine serum albumin (molecular weight: 66,000), ovalbumln (molecular weight: 45,000) and cytochrome C (molecular weight: 13,000), were conducted with the above microspheres as the packing and a 0.2 M phosphate buffer solution (pH: 6.8) as the eluent by means of an ultraviolet absorptiometer (detection wavelength: 280 nm) thereby to obtain the results shown in FIG. 2 without causing any excessive adsorption of the sample. It will be apparent from FIG. 2 that when the packing of the present invention produced in this Example was used, there was obtained an excellent calibration curve for the standard proteins having a molecular weight in the range of $1 \times 10^4$ to $1 \times 10^5$.

Comparative Example 1

The procedure of Example 1 was followed except that the porous spherical carbon particles produced in Example 2 were substituted as the packing for said silicon carbide microspheres, in attempts to analyze the standard polystyrenes (samples). The samples were not eluted since they were too tightly adsorbed on the packing, and no calibration curve was obtained.

Comparative Example 2

The procedure of Example 2 was followed except that the porous spherical carbon particles produced in Example 2 were substituted as the packing for the silicon carbide microspheres, in attempts to analyze the standard proteins (samples). The samples were not eluted since they were too tightly adsorbed on the packing, and no calibration curve was obtained.

EXAMPLE 3

Figure 3:
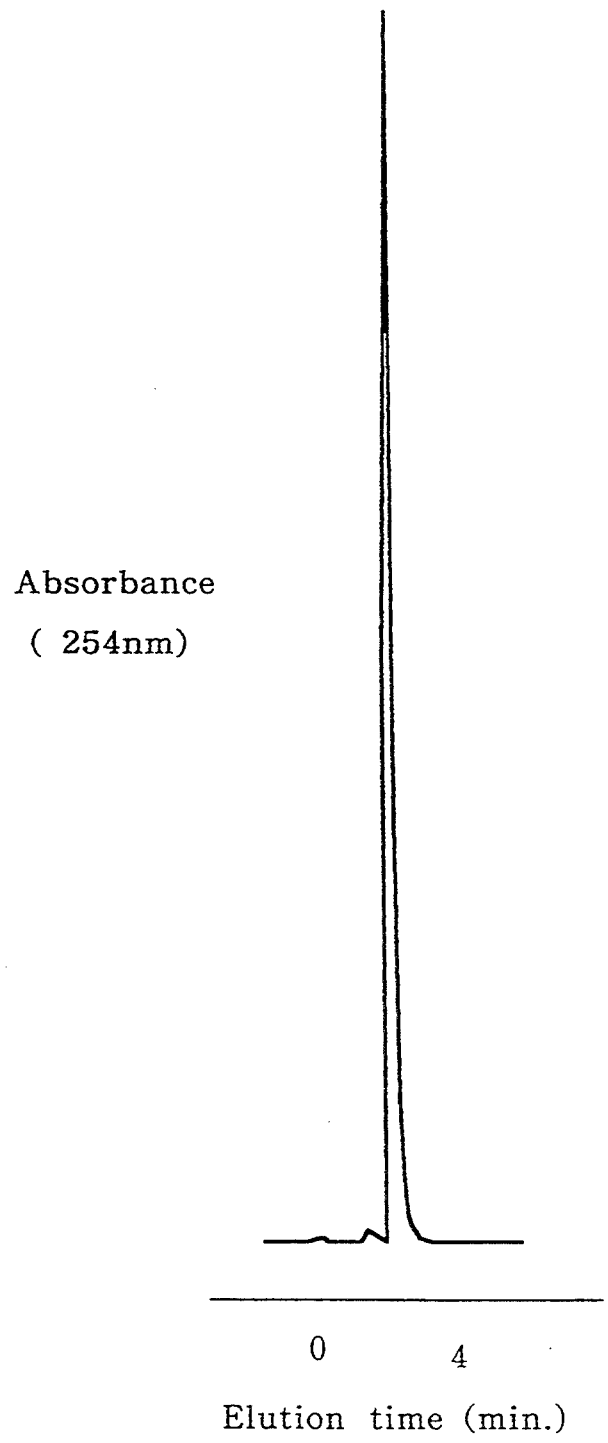
FIG. 3 is a chromatogram showing the elution behavior of naphthalene observed when the packing of the present invention obtained in Example 2 was used.

The silicon carbide microspheres obtained in Example 2 were filled into the same column as that of Example 1. When naphthalene as the sample and then a 30% aqueous acetonltrile solution as the eluent, were poured into the column, excellent elution of the sample was observed without the sample being still adsorbed on the packing. FIG. 3 is a chromatogram showing the elution behavior of naphthalene.

Comparative Example 3

The porous spherical carbon particles obtained in Example 2 were filled into the same column as that of Example 1. When naphthalene as the sample and then a 30% aqueous acetonitrile solution as the eluent, were introduced into the column, the sample was not eluted, since it was too tightly adsorbed on the surface of the packing.

EXAMPLE 4

A polycarbosilane having a number-average molecular weight of 2400 was previously finely divided into particles with a diameter of around 20 μm, and then infusibilized by heating them to 180° C. at a temperature elevation rate of 15° C./h in air. The infusibilized polycarbosilane particles were further divided into ultrafine particles by the use of a jet mill and then classified into particles having a diameter of not larger than 0.5 um. 100 parts by weight of the polycarbosilane powder were mixed with 20 parts by weight of a polycarbosilane (number-average molecular weight: 1500) which had not been infusibilized and 200 parts by weight of toluene. The resultant mixture was passed through a bead mill to obtain a homogeneous slurry. The slurry was granulated with a spray dryer to obtain spherical particles, which were heated to 180° C. at a temperature elevation rate of 15° C./h in air and held at that temperature for 30 min. to infusibilize the particles. Then they were heated to 1500° C. at a temperature elevation rate of 200° C./h in an argon gas atmosphere and held at that temperature for 1 h to bake the particles, thereby converting the polycarbosilane into silicon carbide.

The microspherical particles thus obtained were classified to obtain particles having a diameter of 5 to 15 μm, which were identified as β-SiC by X-ray diffractometry. The results of measurement with a mercury porosimeter indicated that the thus obtained particles had a pore volume of 0.12 ml/g, a specific surface area of 15 m$^2$/g and an average pore diameter of 180 nm. The desorption-side specific surface area was 3.5 m$^2$/g as determined by the BJH method. According to SEM, it was confirmed that the particles were spherical. Therefore, it was concluded that the product was silicon carbide microspheres having numerous through-pores.

The silicon carbide microspheres so produced were filled as the packing into a stainless steel column having an inner diameter of 7.8 mm and a length of 300 mm, and standard polystyrenes (samples) were analyzed with the above microspheres as the packing and tetrahydrofuran or chloroform as the eluent. Excellent calibration curves were obtained for the samples having a molecular weight in the range of $10^4$ to $5 \times 10^6$ when any one of the eluents was used.

The acid and alkali resistances of the above silicon carbide microspheres were evaluated as follows.

A change in elution time (position of elution) of naphthalene was examined with the lapse of time while passing a mixture of a 0.1 M aqueous chloric acid solution and acetonitrile in a volume ratio of 1:1 as the eluent through a stainless steel column packed with the above-described silicon carbide microspheres. Even 120 h after the initiation of passage of the mixture, no change was found in the elution time of naphthalene. Similarly, a change in the naphthalene elution time was examined with the lapse of time while passing a mixture of a 0.1 M aqueous sodium hydroxide solution and acetonitrile in a volume ratio of 1:1 as the eluent through a similar column. Even 100 h after the initiation of passage of the mixture, no change was found in the elution time of naphthalene.

Comparative Example 4

The acid and alkali resistances of a silica gel packing (ODS) having an octadecyl group chemically bonded thereto were evaluated in the same manner as in Example 4.

A change in elution time of naphthalene was examined while passing a mixture of a 0.1 M aqueous chloric acid solution and acetonitrile in a volume ratio of 1:1 as the eluent through a stainless steel column packed with the above-described silica gel packing. 120 hours after the initiation of passage of the mixture, the naphthalene elution time was 85% based on the initial value. Similarly, a change in the naphthalene elution time was examined while passing a mixture of a 0.1 M aqueous sodium hydroxide solution and acetonitrile in a volume ratio of 1:1 as the eluent through a similar column. Two hours after the initiation of passage of the mixture, the peak became broad and a gap was found at the inlet of the column.

Comparative Example 5

Standard polystyrenes (samples) were analyzed by following the procedure of Example 1 except that the above-described silicon carbide microspheres were substituted as the packing for commercially available fine silicon carbide particles having an average diameter of 5 μm (trade name: Green Densic; a product of Showa Denko Co., Ltd.; particles formed by crushing) and having been sized into particles having a diameter of 3 to 8 μm. As a result, all of the samples were eluted at the same time and no excellent calibration curves could be obtained. The fine silicon carbide particles sized above had a specific surface area of 0.52 m$^2$/g and a pore volume of $3 \times 10^{-4}$ ml/g, and scarcely any pore structure was recognized.

EXAMPLE 5

Standard polystyrenes and standard proteins were analyzed by following the procedure of Example 2 except that the silicon carbide microspheres obtained in Example 2 were held at 500° C. in air for 2 h before filling them into the column. Excellent calibration curves similar to those shown in FIG. 2 were obtained.

Comparative Example 6

A commercially available polymer-based packing (trade name: TSK gel G3000H$_8$; styrene/divinylbenzene copolymer produced by Tosoh Corporation; average particle diameter: 10 μm) was held at 500° C. in air for 2 h in the same manner as in Example 5, and the polymer-based packing so treated was tried in vain to be filled into the column because the polymer particles were fused with one another.

(Effects of this invention)

As described above, since the packing of the present invention comprises as a whole the porous silicon carbide having numerous through-pores, the surface thereof is so inert that it does not interact with any sample and it is excellent in thermal and chemical resistances and in stability against any solvents.

Thus, the packing of the present invention is usable as it is for aqueous or non-aqueous GPC thereby to make it possible to separate and analyze various samples, particularly even proteins and compounds having π-electrons, such as polycyclic aromatic compounds, rapidly without fail.

By chemically modifying the surface of the packing of the present invention, there can be obtained various packings for liquid chromatography for various uses such as reversed phase liquid chromatography and ion exchange liquid chromatography. Thus the packing of the present invention is useful also as the base material therefor.

What is claimed is:

1. A process for producing a porous silicon carbide-constituted microspherical packing for liquid chromatography, which comprises the steps of mixing a polycarbosilane, carbon black and a solvent together to obtain a slurry, granulating the slurry into spherical particles, heating the spherical particles to 1450° to 1650° C. at a temperature elevation rate of 100° to 300° C./h in an inert atmosphere to bake the polycarbosilane, and holding the baked spherical particles at 500° to 800° C. in air for 15 to 120 h to remove the carbon black by oxidation.

2. A process according to claim 1, which further comprises the step of infusibilizing the spherical particles by heating them to 110° to 180° C. at a temperature elevation rate of 15° to 30° C./h in air prior to the baking step.

3. A process according to claim 1, which further comprises the step of removing residual $SiO_2$ by washing posterior to the step of removing carbon black.

4. A profess for producing a porous silicon carbide-constituted microspherical packing for liquid chromatography, which comprises the steps of impregnating porous spherical carbon particles with a polycarbosilane, heating the particles thus impregnated to 1450° to 1650° C. at a temperature elevation rate of 100° to 300° C./h in an inert atmosphere to bake the polycarbosilane, and holding the baked particles at 500° to 800° C. in air for 15 to 120 h to remove the carbon portion by oxidation.

5. A process according to claim 4, which further comprises the step of infusibilizing the particles impregnated with the polycarbosilane, by heating them to 110° to 180° C. at a temperature elevation rate of 15° to 30° C./h in air prior to the baking step.

6. A process according to claim 4, which further comprises the step of removing residual $SiO_2$ by washing posterior to the step of removing the carbon portion.

7. A process for producing a porous silicon carbide-constituted microspherical packing for liquid chromatography, which comprises the steps of infusibilizing a polycarbosilane by heating it to 110° to 180° C. at a temperature elevation rate of 15° to 30° C./h in air, pulverizing the infusibilized polycarbosilane into polycarbosilane powder, mixing the polycarbosilane powder with a polycarbosilane and a solvent to obtain a slurry, granulating the slurry into spherical particles, infusibilizing the spherical particles by heating them to 110° to 180° C. at a temperature elevation rate of 15° to 30° C./h in air, and heating the infusibilized particles to 1450° to 1650° C. at a temperature elevation rate of 100° to 300° C./h in an inert atmosphere to bake the polycarbosilane.

8. A process according to claim 7, which further comprises the step of removing residual $SiO_2$ by washing posterior to the baking step.

* * * * *